(12) United States Patent
Maltz et al.

(10) Patent No.: US 7,724,870 B2
(45) Date of Patent: May 25, 2010

(54) DIGITAL TOMOSYNTHESIS IN ROBOTIC STEREOTACTIC RADIOSURGERY

(75) Inventors: Jonathan S. Maltz, Oakland, CA (US); Ali Bani-Hashemi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/130,136

(22) Filed: May 30, 2008

(65) Prior Publication Data

US 2009/0296886 A1   Dec. 3, 2009

(51) Int. Cl.
*A61N 5/10* (2006.01)
*H05G 1/02* (2006.01)
*H01J 31/50* (2006.01)

(52) U.S. Cl. .......................... 378/65; 378/189; 378/197

(58) Field of Classification Search ............... 378/4–20, 378/62, 65, 68, 189, 193, 197, 205; 600/407, 600/425–429; 606/130; 604/20
See application file for complete search history.

(56) References Cited

U.S. PATENT DOCUMENTS

| | | | |
|---|---|---|---|
| 4,340,816 A | 7/1982 | Schott | |
| 4,481,651 A | 11/1984 | Haendle | |
| 4,516,252 A | 5/1985 | Linde et al. | |
| 4,736,396 A | 4/1988 | Boyd et al. | |
| 5,872,828 A | 2/1999 | Niklason et al. | |
| 6,196,715 B1 | 3/2001 | Nambu et al. | |
| 6,483,890 B1 | 11/2002 | Malamud | |
| 6,553,096 B1 | 4/2003 | Zhou et al. | |
| 6,574,629 B1 | 6/2003 | Kaufman et al. | |
| 6,590,958 B2 * | 7/2003 | Barber et al. ............. | 378/98.8 |
| 6,618,467 B1 | 9/2003 | Ruchala et al. | |
| 6,671,349 B1 | 12/2003 | Griffith | |
| 6,778,850 B1 * | 8/2004 | Adler et al. ................ | 600/427 |
| 6,842,502 B2 | 1/2005 | Jaffray et al. | |
| 6,862,337 B2 | 3/2005 | Claus et al. | |
| 6,876,724 B2 | 4/2005 | Zhou et al. | |
| 6,888,919 B2 * | 5/2005 | Graf ............................ | 378/65 |

(Continued)

FOREIGN PATENT DOCUMENTS

EP   1 428 473   6/2004

(Continued)

OTHER PUBLICATIONS

Search Report from (European counterpart, appln. 09155464.2-1269), Aug. 17, 2009, 6 pages.

(Continued)

*Primary Examiner*—Edward J Glick
*Assistant Examiner*—Anastasia Midkiff

(57) ABSTRACT

Some embodiments include a support movable with at least four degrees of freedom, a therapeutic radiation source coupled to the support, a plurality of radiation sources disposed in a fixed relationship to each other, the plurality of radiation sources movable in the fixed relationship with at least four degrees of freedom, a detector to acquire a projection image based on radiation emitted from one of the plurality of radiation sources, and a processor to perform digital tomosynthesis on the projection image acquired by the detector and a plurality of other projection images to generate a cross-sectional image representing a plane viewed from a perspective of the therapeutic radiation source.

12 Claims, 5 Drawing Sheets

U.S. PATENT DOCUMENTS

| | | | |
|---|---|---|---|
| 7,127,028 | B2 | 10/2006 | Sendai |
| 7,200,202 | B2* | 4/2007 | Kusch et al. ............. 378/65 |
| 7,227,925 | B1* | 6/2007 | Mansfield et al. ......... 378/65 |
| 7,245,698 | B2 | 7/2007 | Pang et al. |
| 7,280,633 | B2* | 10/2007 | Cheng et al. ............. 378/65 |
| 7,492,855 | B2 | 2/2009 | Hopkins et al. |
| 7,502,443 | B1* | 3/2009 | Haynes et al. ............ 378/65 |
| 7,519,151 | B1 | 4/2009 | Shukla et al. |
| 7,532,705 | B2 | 5/2009 | Yin et al. |
| 7,567,647 | B1 | 7/2009 | Maltz |
| 2003/0048868 | A1* | 3/2003 | Bailey et al. ............. 378/65 |
| 2005/0251010 | A1 | 11/2005 | Mistretta et al. |
| 2006/0067468 | A1 | 3/2006 | Rietzel |
| 2006/0067473 | A1 | 3/2006 | Eberhard et al. |
| 2006/0098856 | A1 | 5/2006 | Botterweck et al. |
| 2006/0133564 | A1 | 6/2006 | Langan et al. |
| 2006/0193435 | A1* | 8/2006 | Hara et al. .............. 378/65 |
| 2007/0003007 | A1* | 1/2007 | Carrano et al. ........... 378/41 |
| 2007/0009081 | A1 | 1/2007 | Zhou et al. |
| 2007/0291895 | A1 | 12/2007 | Yin et al. |
| 2008/0069420 | A1 | 3/2008 | Zhang et al. |
| 2008/0253516 | A1 | 10/2008 | Hui et al. |
| 2009/0022264 | A1 | 1/2009 | Zhou et al. |

FOREIGN PATENT DOCUMENTS

| | | |
|---|---|---|
| WO | WO 2006/124434 | 11/2006 |
| WO | WO 2007/038306 | 4/2007 |

OTHER PUBLICATIONS

U.S. Appl. No. 12/045,530, Publication No. 2009-0086889).

U.S. Appl. No. 12/130,136.

Maltz, et al., "Fixed Gantry Tomosynthesis System for Radiation Therapy Image Guidance Based on a Multiple Source X-Ray Tube with Carbon Nanotube Cathodes", Medical Physics, vol. 36, No. 5, May 2009, © 2009 Medical Association Physics Medical, pp. 1624-1636.

Vedam, et al., "Acquiring a four-dimensional computed tomography dataset using an external respiratory signal", Dec. 16, 2002, Phys. Med. Biol., vol. 48, pp. 45-62.

Underberg, et al., "Four-dimensional CT scans for treatment planning in stereotactic radiotherapy for stage I lung cancer", Int. J. Radiation Oncology Bio. Phys., Oct. 29, 2004, vol. 60, No. 4, pp. 1283-1290.

Baydush, et al., "Initial application of digital tomosynthesis with on-board imaging in radiation oncology", Conference date Feb. 13, 2005, Proc. SPIE vol. 5745, pp. 1300-1305, Medical Imaging 2005: Physics of medical imaging, Michael J. Flynn, Editor, Apr. 2005.

Rietzel, et al., "Four-dimensional image-based treatment planning: target volume segmentation and dose calculation in the presence of respiratory motion", Apr. 1, 2005, International Journal of Radiation Oncology, vol. 61, No. 5, pp. 1535-1550.

R. Robinson, Nov. 7, 2002, Invitation for sealed bid #638324A, Virginia Polytechnic Institute and State University.

Messaris, et al., "Three-dimensional localization based on projectional and tomographic image correlation: an application for digital tomosynthesis", 1999, Medical Engineering & Physics, 21. pp. 101-109.

Dobbins, III, James T., et al., "Digital X-Ray Tomosynthesis: Current State of the Art and Clinical Potential", Institute of Physics Publishing, Physics in Medicine and Biology; Phys. Med. Biol. 48 (2003), pp. R65-R106 © 2003 IOP Publishing Ltd.

Louwe, R. J. W., et al., "Three-dimensional dose reconstruction of breast cancer treatment using portal imaging", The Netherlands Cancer Institute/Antoni van Leeuwénhoek Hospital, Dept. of Radiotherapy, Amsterdam, The Netherlands, pp. 2376-2389, Med. Phys. 30 (9), Sep. 2003, © Am. Assoc. Phys. Med.

"Mega Voltage Cone Beam Reconstruction", http://www.ucsf.edu/ipouliot/Course/Lession22.html, Jun. 7, 2006.

Lalush, et al., "Three-Dimensional Tomosynthesis Reconstruction from 1D and 2D X-Ray Source Arrays", Nuclear Science Symposium Conference Record, 2006; IEEE, PI Oct. 1, 2006, pp. 1670-1673.

PCT Search Report, Feb. 2, 2009, 4 pages.

PCT Written Opinion, Feb. 2, 2009, 4 pages.

U.S. Appl. No. 12/045,530, filed Mar. 10, 2008.

* cited by examiner

US 7,724,870 B2

DIGITAL TOMOSYNTHESIS IN ROBOTIC STEREOTACTIC RADIOSURGERY

BACKGROUND

1. Field

The embodiments described below relate generally to systems for delivering radiation treatment. More specifically, some embodiments are directed to treatment verification systems used in conjunction with such delivery.

2. Description

Conventional radiotherapy systems direct a beam of photon, proton, neutron, or other radiation toward a target volume of a patient. The radiation destroys cells within the target volume by causing ionizations within the cells or other radiation-induced cell damage.

Isocentric radiotherapy is typically delivered by a therapeutic radiation source integrated into a rotatable gantry. The gantry rotates around a horizontal axis such that a radiation beam emitted from the therapeutic radiation source passes through a same volume of space (i.e., an isocenter) at each angle of rotation. A target volume of a patient is therefore positioned at the isocenter prior to emission of the beam and rotation of the gantry. Due to physical constraints, isocentric treatment is particularly suited to target volumes located above the chest region.

Multi-jointed robotic arms are typically used to deliver non-isocentric radiation treatment. Such arms include an integrated therapeutic radiation source and provide more flexible positioning with respect to a patient in order to deliver treatment radiation from any angle to a target volume located virtually anywhere within the patient. Non-isocentric radiation treatment may therefore irradiate the target volume from fewer external positions than those used during isocentric radiation treatment. Accordingly, non-isocentric treatment may be required in order to avoid irradiating sensitive healthy structures.

In both isocentric and non-isocentric treatment modes, the target volume and the radiation source must be registered to one another in three-dimensional space so as to ensure delivery of the radiation according to a treatment plan. Errors in radiation delivery can result in low irradiation of tumors and high irradiation of sensitive healthy tissue. Positioning accuracy may be particularly problematic in the case of non-isocentric treatment, since up to six degrees of freedom may be available. All six degrees of freedom may be necessary to irradiate a certain spatial position (x, y, z) within the target volume from an arbitrary direction orientation (yaw, pitch, roll).

The GammaKnife® radiosurgical system by Elekta employs Cobalt-60 radiation sources which are fixed in space. An anatomical target (e.g., a volume within a patient's head) is moved and registered to the focal point of radiation sources. This scenario requires the rigid fixation of the patient's skull within a pin based stereotactic frame, with substantial discomfort to the patient. By relocating the frame within the system, the patient's skull is repeatedly repositioned relative to the fixed radiation reference frame based on a pre-calculated radiation plan.

Some radiosurgery systems avoid such fixed-frame positioning by using external markers on the patient as well as markers internal the patient. Spatial correlation between the external markers and the internal markers is established by an X-ray image showing both sets of markers. Positions of the external markers are tracked during treatment and, based on the predetermined spatial correlation, corresponding positions of the internal markers are determined. The accuracy of the latter determination is limited due to the variability of the actual correlation between the external and internal markers.

What is needed is improved determination of a target position within a robotic stereotactic radiosurgery system.

SUMMARY

In order to address the foregoing, some embodiments provide a support movable with at least four degrees of freedom, a therapeutic radiation source coupled to the support, a plurality of radiation sources disposed in a fixed relationship to each other, the plurality of radiation sources movable in the fixed relationship with at least four degrees of freedom, and a detector to acquire a projection image based on radiation emitted from one of the plurality of radiation sources. A processor is included to perform digital tomosynthesis on the projection image acquired by the detector and a plurality of other projection images to generate a cross-sectional image representing a plane viewed from a perspective of the therapeutic radiation source.

The plurality of radiation sources may be coupled to the support, and the detector may be coupled to a second support movable with at least four degrees of freedom. According to some aspects, the plurality of radiation sources are coupled to a second support movable with at least four degrees of freedom, and the detector is coupled to the support. Some embodiments further provide a plurality of other detectors coupled to the support, wherein the plurality of other detectors are to acquire the plurality of other projection images based on radiation emitted from respective ones of a plurality of the plurality of radiation sources.

Some aspects may include a second support movable with at least four degrees of freedom, wherein the plurality of radiation sources are coupled to the second support, and a third support movable with at least four degrees of freedom, wherein the detector is coupled to the third support.

Still further aspects may include a method in which a therapeutic radiation source is moved through at least four degrees of freedom to a first position, a plurality of radiation sources disposed in a fixed relationship are moved through at least four degrees of freedom to a second position, and a detector is moved through at least four degrees of freedom to a third position. Radiation is emitted from one of the plurality of radiation sources at the second position, a projection image is acquired with the detector based on the emitted radiation at the third position, and digital tomosynthesis is performed on the projection image and a plurality of other projection images to generate a cross-sectional image representing a plane viewed from a perspective of the first position of the therapeutic radiation source.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
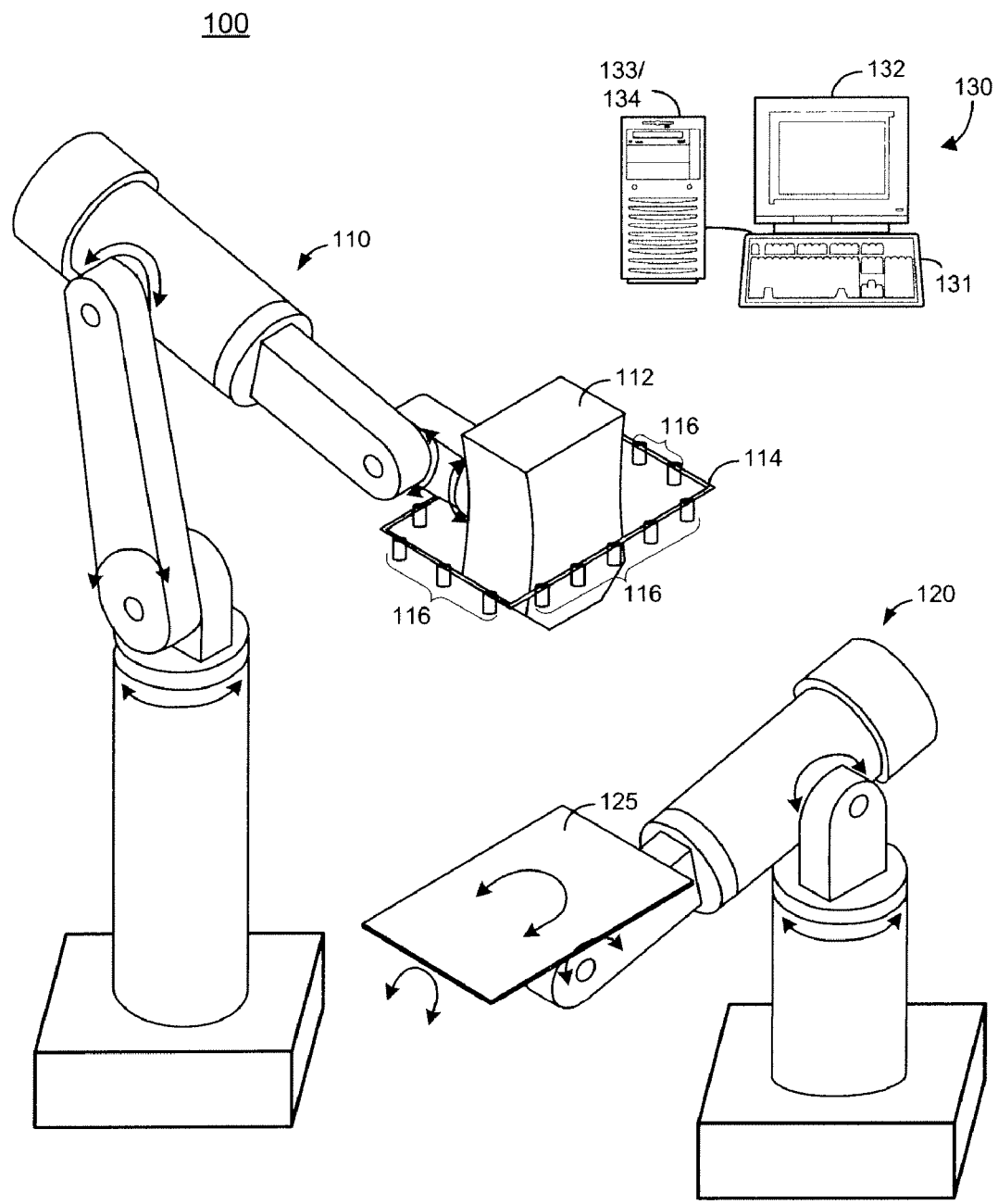
FIG. 1 is a perspective view of a treatment room according to some embodiments.

FIG. 1 is a perspective view of treatment room 100 according to some embodiments. Located within treatment room 100 are first support 110, second support 120 and operator console 130. The elements of treatment room 100 may be used in some embodiments to verify a patient position and to perform robotic stereotactic radiosurgery on such a patient. More particularly, some embodiments comprise performance of digital tomosynthesis to verify a patient position and emission of a therapeutic radiation beam toward the patient according to a treatment plan.

First support 110 may comprise a multi-jointed robotic arm movable in the directions indicated by the illustrated arrows. Examples of a multi-jointed robotic arm include, but are not limited to, a robotic arm such as that used in the Cyberknife® system by Accuray®. Such movement may reflect at least four degrees of freedom in some embodiments. Therapeutic radiation source 112 is coupled to first support 110 in some embodiments. Movement of first support 110 therefore results in corresponding movement of radiation source 112.

The illustrated coupling between radiation source 112 and first support 110 provides rotation of source 112 with respect to support 110. In some embodiments, this coupling may comprise a ball joint or other type of coupling to provide other types of movement to source 112 relative to support 110.

Therapeutic radiation source 112 may comprise a linear accelerator to emit a beam of photon radiation or electron radiation having various energies. Therapeutic radiation source 112 may also or alternatively comprise radioisotope sources, cobalt-60 radiation sources, or other non-linac sources that are or become known.

Therapeutic radiation source 112 may include a beam-shielding device, or collimator, for shaping the beam and for shielding sensitive surfaces from the beam. The collimator may be rotated and various elements of the collimator may be positioned according to a treatment plan. The collimator may thereby control a cross-sectional shape of the beam. Such a collimator may be particularly useful in a case that source 112 emits a beam exhibiting significant geometric divergence. In some embodiments, however, source 112 emits a substantially columnar beam.

Mount 114 is coupled to support 110 and or radiation source 112. Support 114 includes an array of radiation sources 116. Radiation sources 116 may comprise any sources to emit kilovoltage radiation or other imaging radiation that is or becomes known. In some embodiments, radiation sources 116 employ carbon nanotube cathode-based radiation emission. Radiation sources 116 are affixed to support 114 such that each radiation source 116 is disposed in a fixed relationship to each other radiation source 116. Moreover, in some embodiments, each radiation source 116 is disposed in a fixed relationship with respect to a beam emitted from radiation source 112. Movement of first support 110 may therefore cause movement of radiation source 112, mount 114 and radiation sources 116 while maintaining the relative fixed relationship therebetween.

Second support 120 may comprise a multi-jointed robotic arm movable in the directions indicated by the arrows shown thereon. The movement of second support 120 may reflect at least four degrees of freedom in some embodiments. Second support 120 is coupled to detector 125. According to the illustrated embodiment, the coupling of detector 125 to support 120 provides roll, pitch and yaw movement of detector 125 with respect to second support 120.

Detector 125 may acquire projection images before, during and/or after radiation treatment. For example, detector 125 may be used to acquire projection images for verification and recordation of a target volume position and of an internal patient portal to which radiation is delivered. Detector 125 may comprise any system to acquire an image based on received radiation.

In some embodiments, detector 125 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge. The stored charge therefore comprises an acquired image that represents intensities at each location of a radiation field produced by a radiation beam. The bounds of the radiation field are determined by the physical intersection of the radiation beam with the surface of the scintillator layer.

Detector 125 may comprise other types of imaging devices. For example, incoming radiation may also be converted to and stored as electrical charge without use of a scintillator layer. In such imaging devices, radiation is absorbed directly by an array of amorphous selenium photoconductors. The photoconductors convert the radiation directly to stored electrical charge that comprises an acquired image of a radiation field.

Operator console 130 includes input device 131 for receiving instructions from an operator and output device 132, which may be a monitor for presenting operational parameters radiation source 112, images acquired by detector 125, CT images used for treatment planning, cross-sectional digital tomosynthesis images, interfaces for receiving operator instructions, and/or operator alerts. According to some embodiments, output device 132 may present an alert notifying an operator of a positioning error prior to or during treatment delivery.

Input device 131 and output device 132 are coupled to processor 133 and storage 134. Processor 133 may execute program code to perform any of the determinations and generations described herein, and/or to cause linac 110 to perform any of the process steps described herein. For example, processor 133 may perform digital tomosynthesis on a projection image acquired by detector 125 and a plurality of other projection images to generate a cross-sectional image representing a plane viewed from a perspective of therapeutic radiation source 112. Such planes of interest typically lie perpendicular to the central axis of the treatment beam.

Storage 134 may also store program code to generate and/or modify a treatment plan according to some embodiments. Accordingly, storage 134 may also store radiation treatment plans in accordance with any currently- or hereafter-known format. The treatment plans may comprise scripts that are automatically executable by elements of room 100 to provide treatment fractions. Each beam of each fraction of each treatment plan may require radiation source 112 to be positioned in a particular manner with respect to a patient.

A hardware environment according to some embodiments may include less or more elements than those shown in FIG.

Figure 2:
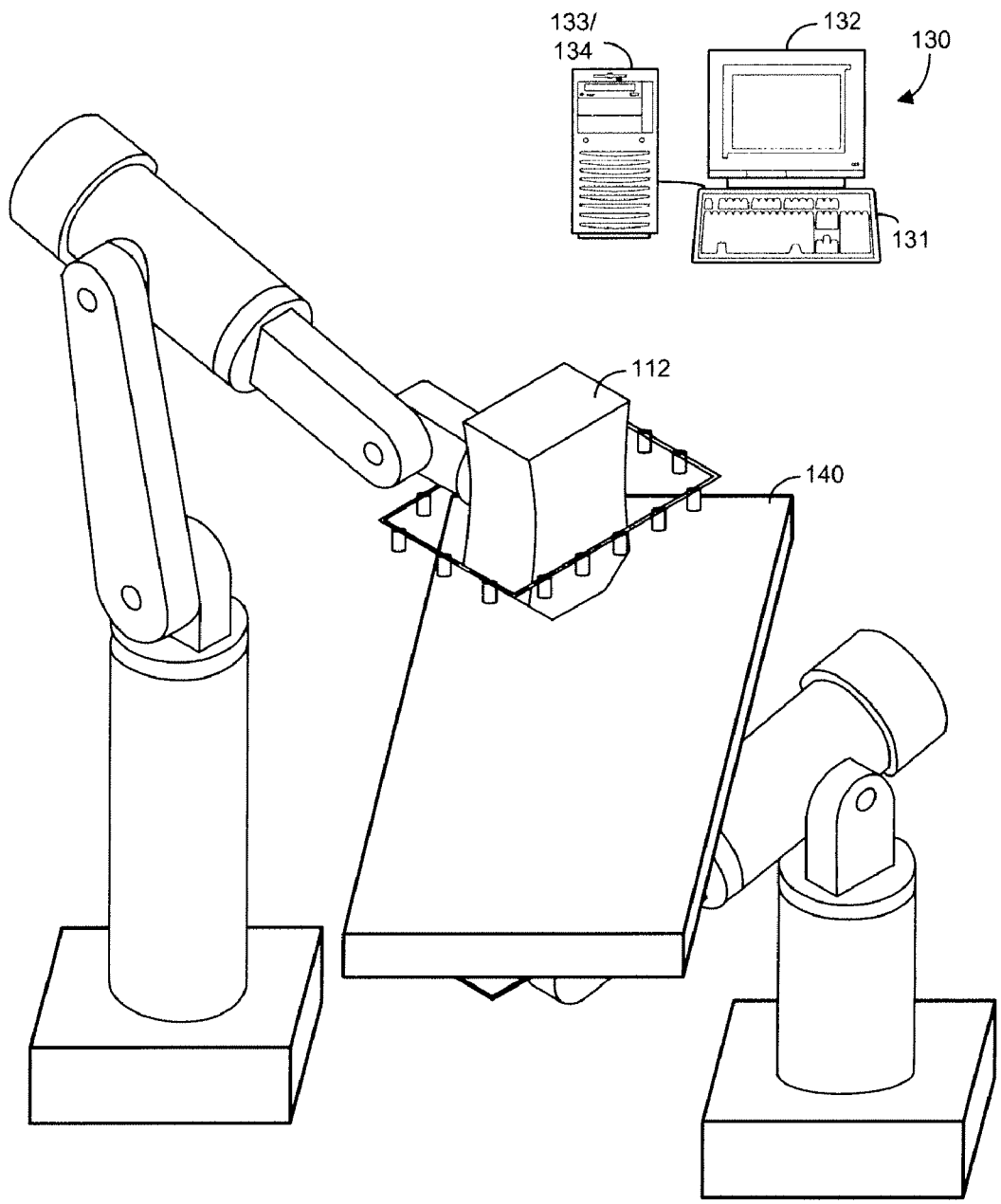
FIG. 2 is a perspective view of a treatment room according to some embodiments.

1. For purposes of clarity, for example, FIG. 1 does not include an element for supporting a patient before and during treatment. FIG. 2 therefore shows treatment room 100 including table 140. Table 140 may be adjustable to assist positioning a target volume with respect to radiation source 112.

Unshown elements may be required to provide AC power, RF power, cooling, hydraulics, vacuum and/or other systems needed to operate support 110, source 112, sources 116, support 120, detector 125 and table 140. In addition, embodiments are not limited to the illustrated elements and/or environment.

According to some embodiments, a patient is placed on table 140 and first support 110 moves radiation source 112 to a treatment position dictated by a treatment plan. Such movement also moves radiation sources 116 to a particular position by virtue of their coupling to radiation source 112. Second support 120, in turn, moves detector 125 to a position facing therapeutic radiation source 112 and on an opposite side of the patient from therapeutic radiation source 112.

Each of radiation sources 116 successively emits radiation toward detector 125. Detector 125 acquires a projection image based on each successive emission. More particularly, detector 125 develops and stores charge representing radiation intensities at each location of a radiation field produced by each successive emission. Since the patient is located between sources 116 and detector 125, the radiation intensity at a particular location represents the attenuative properties of tissues along a divergent line between the emitting source 116 and the particular location. A set of radiation intensities acquired by detector 125 in response to a particular emission may therefore comprise a two-dimensional projection image of these tissues.

Such a projection image, taken alone, is of limited use in determining a position of a particular internal target. Specifically, a target within the patient will likely be obscured by structures located between the target and radiation sources 116 and by structures located between the target and detector 125. Processor 133 of computer system 130 therefore performs digital tomosynthesis on the projection images to generate a cross-sectional image of the target. The cross-sectional image represents a particular plane of the patient viewed from a particular perspective (e.g., the perspective of radiation source 112).

Figure 3:
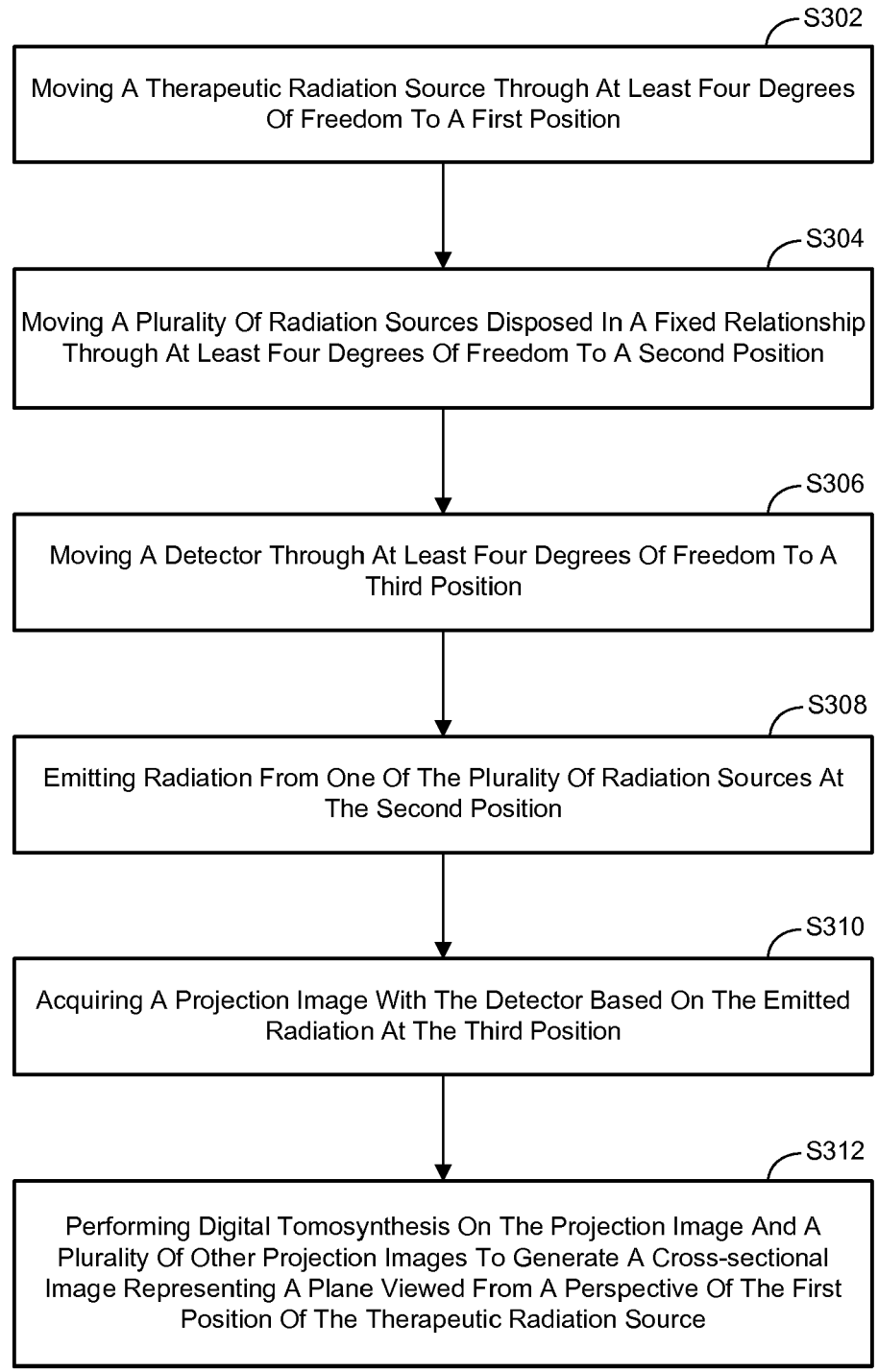
FIG. 3 is a flow diagram of process steps pursuant to some embodiments.

FIG. 3 is a flow diagram of a process according to some embodiments. Process 300 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, or a signal. Examples of these processes will be described below with respect to the elements of treatment room 100, but embodiments are not limited thereto.

Process 300 may be performed after a patient has been placed on a treatment table and is awaiting treatment. At S302, a therapeutic radiation source is moved through at least four degrees of freedom to a first position. In one example of S302, first support 110 moves radiation source 112 to a treatment position dictated by a treatment plan.

The treatment plan may define multiple treatment fractions, each of which includes one or more discrete beams to be delivered. For each beam, the treatment plan may specify a location and delivery angle of radiation source 112, and a cross-sectional image of a desired target orthogonal to a beam axis. The cross-sectional image may be generated based on a CT image used to create the treatment plan.

A plurality of radiation sources disposed in a fixed relationship is moved at S304. The sources are moved through at least four degrees of freedom to a second position. Continuing the present example, the movement of source 112 at S302 causes movement of radiation sources 116 to a particular position dictated by the fixed relationship of radiation sources 116 to radiation source 112. Accordingly, in the present example, S302 and S304 occur simultaneously.

Next, at S306, a detector is moved through at least four degrees of freedom to a third position. According to one example of S306, second support 120 moves detector 125 to a position facing therapeutic radiation source 112 and on an opposite side of the patient from therapeutic radiation source 112. Detector 125 may be positioned such that a beam axis of therapeutic radiation source 112 is orthogonal to an incoming surface of detector 125.

Radiation is emitted from one of the plurality of radiation sources at S308. The radiation may be emitted from one of radiation sources 116 from the second position to which the source 116 was moved at S304. Next, at S310, a projection image is acquired based on the emitted radiation. Detector 125 may develop, store and output a projection image corresponding to the emitted radiation. The projection image may comprise a two-dimensional set of radiation intensities representing the attenuative properties of tissues between the radiation source 116 and detector 125.

Digital tomosynthesis is performed on the projection image at S312 together with a plurality of other projection images to generate a cross-sectional image. The cross-sectional image represents a plane viewed from a perspective of the therapeutic radiation source at the first position.

S308 and S310 may be performed several times in succession prior to S312 in order to obtain the plurality of other projection images. For example, radiation may be emitted from one of radiation sources 116 at S308 and a corresponding projection image may be acquired at S310, radiation may emitted from another of radiation sources 116 and another corresponding projection image may be acquired at S310, and so on until radiation has been emitted from each of the plurality of radiation sources and corresponding projection images have been acquired.

Various digital tomosynthesis reconstruction algorithms have been developed, which include filtered back projection algorithms. For example, the projection images may be filtered with a Ram-Lak filter before back projection. Such algorithms are particularly suitable for digital tomosynthesis reconstruction when the radiation sources are located along an arc segment, as is the case for conventional isocentric tomography.

According to some embodiments, radiation sources 116 may be disposed in a circular configuration, an elliptical configuration, a triangular configuration, a square configuration, a rectilinear configuration, and/or along the sides of any polygon. Since radiation sources 116 in such configurations might not lie along an arc subtended from a common point, more general methods of tomosynthesis reconstruction may be employed. For example, S312 may include an iterative reconstruction method such as the algebraic reconstruction technique (ART), the simultaneous algebraic reconstruction technique (SART), the simultaneous iterative reconstruction technique (SIRT) or the ordered subsets expectation maximization (OSEM) algorithm. More generally, any methods that solve for the values of the voxels within the imaged field-of-view based on the measured projection values are suitable for tomosynthesis reconstruction. Such methods include techniques of optimization and/or regression, and may be applied to maximize certain characteristics (e.g., statistical likelihood, statistical entropy) and/or to minimize others (e.g., the sum of squared residuals).

The projection images acquired at S310 may be corrected or transformed based on characteristics of detector 125 and/or based on the fixed relationship between detectors 116. In the latter regard, the projection images may be modified to account for the different distances over which different portions of the emitted beams travel to reach detector 125.

Process 300 may therefore provide a reconstructed partial cross-sectional image that is orthogonal to the principal beam axis of a radiation source at a particular delivery angle. The reconstructed image may include a target volume, if the geometry of projection image acquisition includes the target. In comparison to two-dimensional projection images alone, digital tomosynthesis provides improved delineation of depth-resolved tissue boundaries due to the reduced influence of under- and overlying structures.

The reconstructed partial cross-sectional image could then be compared with an expected cross-sectional image generated based on the treatment plan. For example, a three-dimensional CT image is loaded into a treatment planning system and a treatment plan is created based on the image. A delivery vector is determined for one or more treatment beams of each treatment fraction of the treatment plan. For each delivery vector, a set of projection images is generated using a divergent virtual source-detector model (e.g., such as that used for a Digitally Reconstructed Radiograph (DRR)). The set of projection images simulates the projection images described above with respect to process 300. The expected cross-sectional image for a particular delivery vector is then generated by applying digital tomosynthesis to the set of projection images generated for the particular delivery vector.

Therapeutic radiation source 112 may deliver a radiation beam after S312 according to the treatment plan if the comparison of the cross-sectional images meets predefined criteria. In some examples, flow returns to S302 after delivery of the radiation beam. Therapeutic radiation source 112, sources 116 and detector 125 may then be moved to new positions dictated by the treatment plan at S302, S304 and S306 for delivery of a next treatment fraction.

Figure 4:
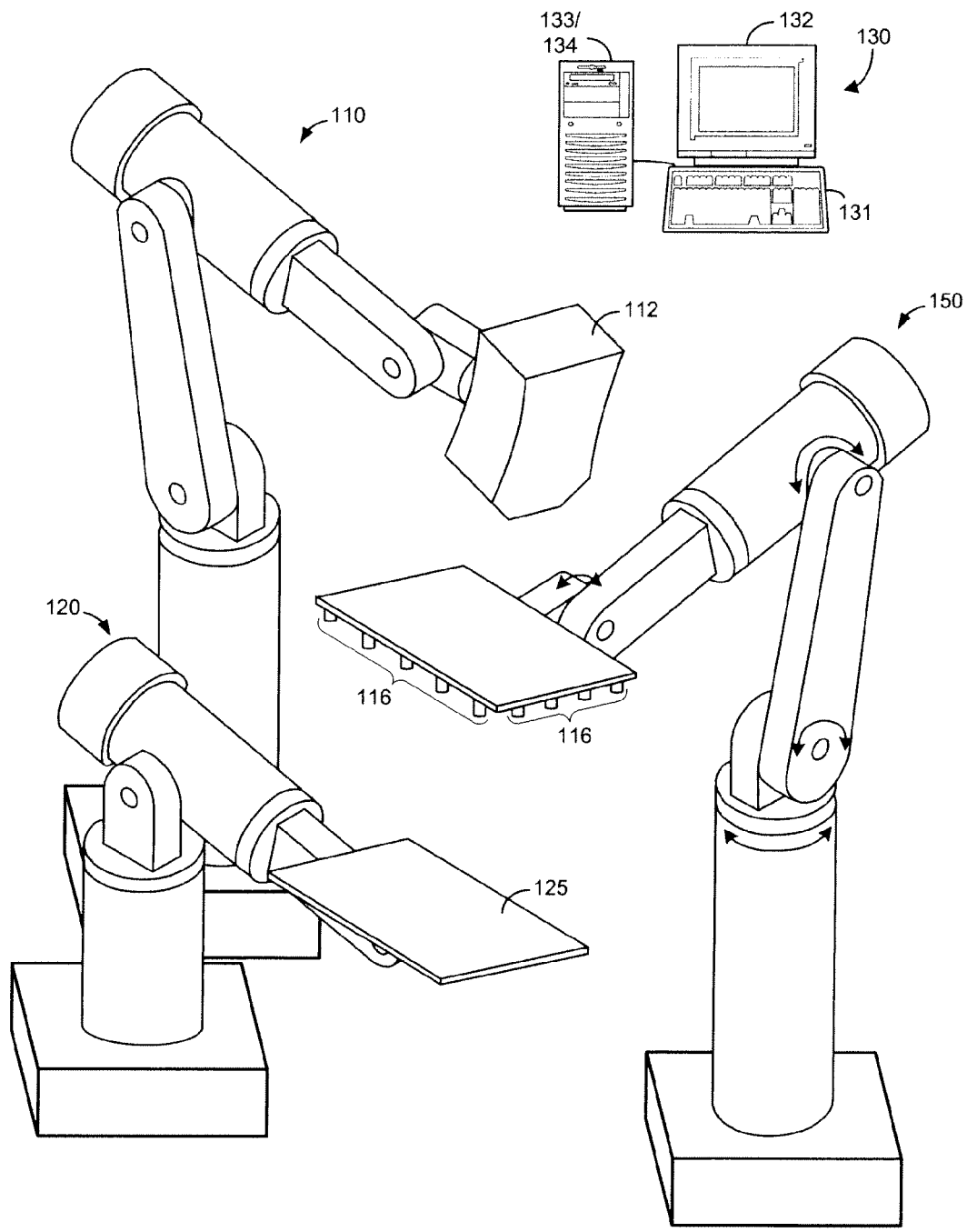
FIG. 4 is a perspective view of a treatment room according to some embodiments.

Embodiments are not limited to those in which S302 and S304 occur simultaneously. FIG. 4, for example, illustrates an embodiment including movable support 110 coupled to therapeutic radiation source 112 and movable support 120 coupled to detector 125 as described above with respect to FIG. 1.

FIG. 4 also illustrates separate movable support 150 coupled to radiation sources 116. Movable support 150 may also comprise a multi-jointed robotic arm movable through at least four degrees of freedom. Radiation sources 116 of FIG. 4 are disposed in a fixed relationship relative to one another. Radiation sources 116 may be coupled to support 150 so as to provide roll, pitch and yaw movement of source 116 with respect to support 150.

Accordingly, radiation sources 116 of FIG. 4 may be moved independently of therapeutic radiation source 112 and detector 125. As a result, S302 and S304 may be performed either simultaneously or consecutively.

Figure 5:
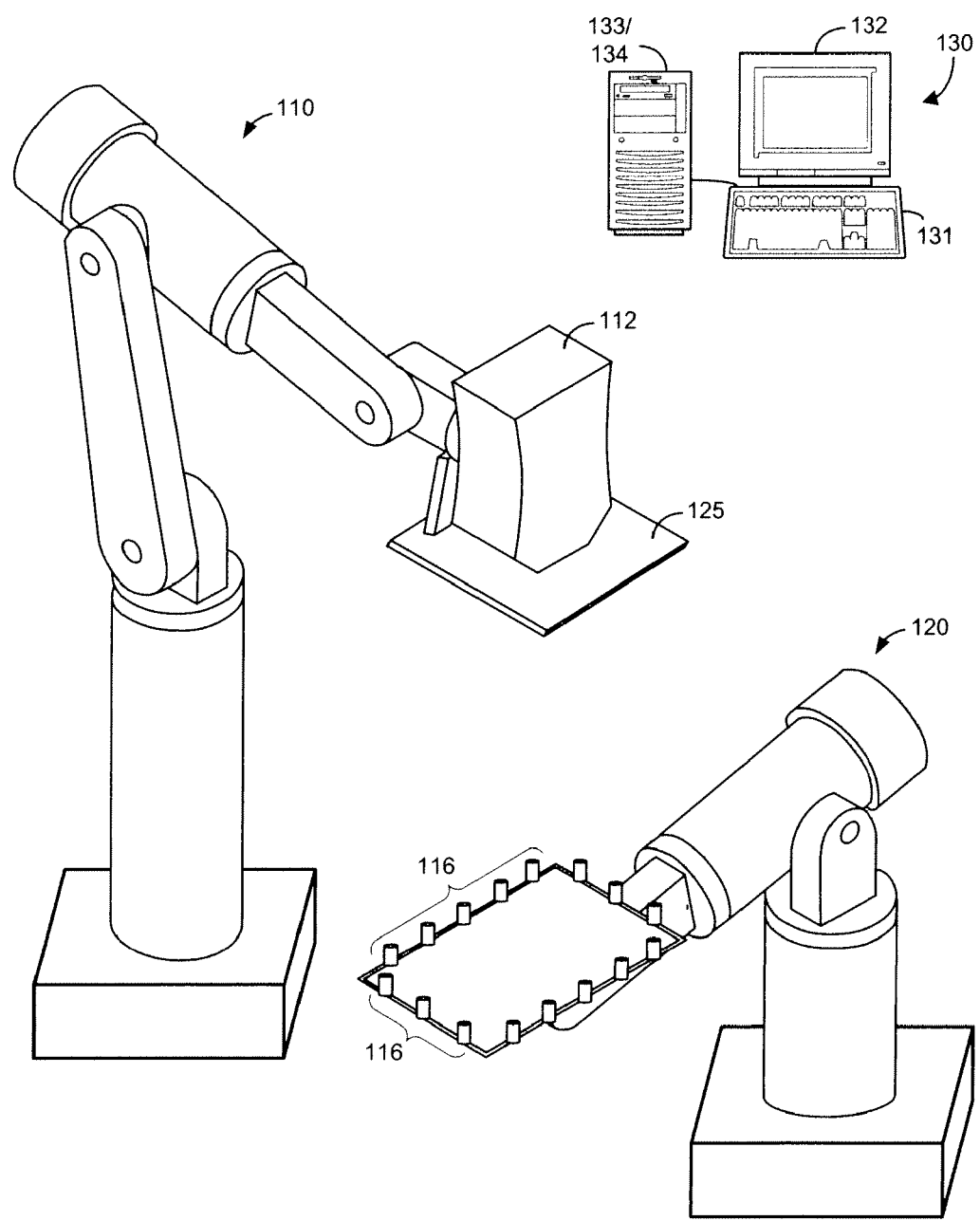
FIG. 5 is a perspective view of a treatment room according to some embodiments.

FIG. 5 illustrates an embodiment in which both therapeutic radiation source 112 and detector 125 are coupled to first support 110. Radiation sources 116 are shown coupled to support 120. If used to implement process 300, movement of support 110 would cause S302 and S306 to occur simultaneously. Also, it may be desirable or necessary to move detector 125 out of a beam path of therapeutic radiation source 112 prior to delivery of treatment radiation.

Despite the exchanged positions of sources 116 and detector 125 with respect to FIG. 1, the FIG. 5 embodiment may provide a reconstructed partial cross-sectional image that is orthogonal to the principal beam axis of radiation source 112 at a particular delivery angle.

The several embodiments described herein are solely for the purpose of illustration. Therefore, persons in the art will recognize from this description that other embodiments may be practiced with various modifications and alterations.

What is claimed is:

1. An apparatus comprising:
   a support movable with at least four degrees of freedom;
   a therapeutic radiation source coupled to the support;
   a plurality of radiation sources disposed in a fixed relationship to each other, the plurality of radiation sources movable in the fixed relationship with at least four degrees of freedom;
   a second support movable with at least four degrees of freedom, wherein the second support is movable with the at least four degrees of freedom independent of the first support and not coupled to the first support;
   a detector to acquire a projection image based on radiation emitted from one of the plurality of radiation sources, wherein the detector is coupled to the second support; and
   a processor to perform digital tomosynthesis on the projection image acquired by the detector and a plurality of other projection images to generate a cross-sectional image representing a plane viewed from a perspective of the therapeutic radiation source.

2. An apparatus according to claim 1, wherein the plurality of radiation sources are coupled to the support.

3. An apparatus according to claim 2, the detector to acquire the plurality of other projection images based on radiation emitted from respective ones of a plurality of the plurality of radiation sources.

4. An apparatus according to claim 3, further comprising:
   a second support movable with at least four degrees of freedom, wherein the detector is coupled to the second support.

5. An apparatus according to claim 1, wherein:
   the plurality of radiation sources are coupled to the second support.

6. An apparatus according to claim 4, further comprising:
   a plurality of other detectors coupled to the second support, wherein the plurality of other detectors are to acquire the plurality of other projection images based on radiation emitted from respective ones of a plurality of the plurality of radiation sources.

7. An apparatus according to claim 1, further comprising:
   a third support movable with at least four degrees of freedom, wherein the plurality of radiation sources are coupled to the third support.

8. A method comprising:
   moving a therapeutic radiation source through at least four degrees of freedom to a first position;
   moving a plurality of radiation sources disposed in a fixed relationship through at least four degrees of freedom to a second position;
   moving a detector through at least four degrees of freedom to a third position independent of the moving of the therapeutic radiation source through the at least four degrees of freedom of the therapeutic radiation source;
   emitting radiation from one of the plurality of radiation sources at the second position;
   acquiring a projection image with the detector based on the emitted radiation at the third position; and
   performing digital tomosynthesis on the projection image and a plurality of other projection images to generate a cross-sectional image representing a plane viewed from a perspective of the first position of the therapeutic radiation source.

9. A method according to claim 8, wherein the therapeutic radiation source and the plurality of radiation sources are coupled to a same support and the steps of moving the therapeutic radiation source and moving the plurality of radiation sources occur simultaneously.

10. A method according to claim 9, further comprising:

emitting radiation from respective ones of a plurality of other radiation sources at the second position; and acquiring the plurality of other projection images with the detector based on the radiation emitted from the respective ones of the plurality of other radiation sources at the second position.

11. A method according to claim 8, wherein moving the detector through at least four degrees of freedom to a third position comprises:

moving a plurality of other detectors through at least four degrees of freedom, wherein the plurality of other detectors are coupled to the same support, and further comprising:

emitting radiation from other ones of the plurality of other radiation sources at the second position; and acquiring the plurality of other projection images with the plurality of other detectors based on the radiation emitted from the respective ones of the plurality of other radiation sources at the second position.

12. A method according to claim 8, wherein the therapeutic radiation source is coupled to a first support, the plurality of radiation sources are coupled to a third support, and the detector is coupled to the second support, and wherein the therapeutic radiation source, the plurality of radiation sources, and the detector are moved independently of one another.

\* \* \* \* \*